United States Patent [19]

Ogawa et al.

[11] 4,138,365

[45] Feb. 6, 1979

[54] CATALYST FOR THE MANUFACTURE OF METHACRYLIC OR ACRYLIC ACID

[75] Inventors: Masanobu Ogawa; Toshitake Kojima, both of Takasaki, Japan

[73] Assignee: Nippon Kayaku Kabushiki Kaisha, Tokyo, Japan

[21] Appl. No.: 758,352

[22] Filed: Jan. 10, 1977

[30] Foreign Application Priority Data

Nov. 27, 1976 [JP] Japan .................................. 51-141784

[51] Int. Cl.$^2$ .......................... B01J 27/14; C07C 51/24
[52] U.S. Cl. .................................... 252/435; 252/437; 562/534
[58] Field of Search ............................. 252/435, 437; 260/530 N

[56] References Cited

U.S. PATENT DOCUMENTS

| | | | |
|---|---|---|---|
| 3,554,931 | 1/1971 | Brown | 252/461 X |
| 3,579,574 | 5/1971 | Van der Meer | 252/475 X |
| 3,704,317 | 11/1972 | Yamashita et al. | 252/461 X |
| 3,792,086 | 2/1974 | Frank et al. | 252/437 X |
| 3,976,688 | 8/1976 | Akiyama et al. | 260/530 N |
| 4,001,316 | 1/1977 | Ishimi | 260/530 N |
| 4,042,623 | 8/1977 | Ogawa | 252/435 X |

FOREIGN PATENT DOCUMENTS

1362068 7/1974 United Kingdom.

*Primary Examiner*—Delbert E. Gantz
*Assistant Examiner*—William G. Wright
*Attorney, Agent, or Firm*—Russell & Nields

[57] ABSTRACT

A catalyst comprising (1) palladium, (2) phosphorus, (3) antimony, (4) X and (5) oxygen wherein X denotes at least one element selected from the group consisting of potassium, sodium, rubidium, lithium, cerium, beryllium, magnesium, calcium, vanadium, strontium, zinc, thorium and rhenium.

There is also provided a process for the manufacture of methacrylic or acrylic acid by oxidizing methacrolein or acrolein with molecular oxygen in the vapor phase in the presence of the catalyst defined above.

2 Claims, No Drawings

CATALYST FOR THE MANUFACTURE OF METHACRYLIC OR ACRYLIC ACID

This application is related to our co-pending application, Ser. No. 646,375, filed Jan. 2, 1976 and assigned to the assignee of the present application.

BACKGROUND OF THE INVENTION

This invention relates to a process for the production of methacrylic or acrylic acid by oxidizing methacrolein or acrolein and to a catalyst.

More particularly, this invention relates to a process for the production of methacrylic or acrylic acid by oxidizing methacrolein or acrolein with molecular oxygen in the presence of steam by using a catalyst comprising (1) palladium, (2) phosphorus, (3) antimony, (4) X and (5) oxygen wherein X denotes at least one element selected from the group consisting of potassium, sodium, rubidium, lithium, cerium, beryllium, magnesium, calcium, vanadium, strontium, zinc, thorium and rhenium, and to the catalyst.

The process of the invention may further comprise supplying into the reaction system a phosphoric acid or a phosphorus compound capable of forming a phosphoric acid through a chemical change during the reaction.

For the synthesis of methacrylic acid by oxidizing methacrolein in a vapor phase a number of catalysts have hitherto been proposed.

Almost all of these catalysts, however, have low activities. Further, if the reaction is carried out at an elevated temperatures in order to increase the conversion, large amounts of undesirable by-products such as carbon monoxide, carbon dioxide, acetic acid etc. are produced so that the per-pass yield of methacrylic acid is very low.

The catalysts as disclosed in the Japanese Patent Laid-Open Publication Nos. 67216/1973 and 61416/1973, which are improved in their catalytic activity and selectivity, comprise phosphomolybdic acid or its salts as a main ingredient.

Phosphomolybdic acid-based catalysts have a disadvantage that the catalyst lifetime is short. Once they lose activity, the activity of these catalysts cannot be restored by means of a simple treatment such as re-calcination, for example. When the temperature of reaction or calcination exceeds 450° C., they are abruptly degraded in catalytic activity. Thus, they are thermally unstable and they are not always available for commercial use.

Further, conventional phosphomolybdic acid-based catalysts offer a notably short catalytic lifetime when the reaction is carried out at a particularly high space velocity.

From a commercial aspect, it is desired to develop a catalyst which has acceptable activity and selectivity at low temperatures as well as a longer service life. Particularly desirable is a catalyst which can maintain its activity over a long period of time even when the reaction is carried out at high space velocities.

DESCRIPTION OF THE INVENTION

The inventors have made a study on the manufacture of methacrylic and acrylic acids, particularly on a catalyst suitable for their manufacture and the influence thereon, in order to obviate the above-described disadvantages of the prior art and have found a process for the production of methacrylic or acrylic acid from methacrolein or acrolein wherein not only the conversion of methacrolein or acrolein is high, but also the selectivity of methacrylic or acrylic acid produced is high at low temperatures and a novel catalyst therefor which has a longer service life even under the condition of a high space velocity.

According to the present invention, not only methacrolein or acrolein is susceptible to oxidation at low temperatures and methacrylic or acrylic acid is produced in high yields, but also the formation of by-products such as acetic acid, carbon monoxide and carbon dioxide owing to the degradation is well suppressed. In addition the catalyst according to the present invention is thermally stable and therefore has a substantially longer service life, particularly even when the reaction is carried out at high space velocities.

The catalyst of the present invention comprises (1) palladium, (2) phosphorus, (3) antimony, (4) X and (5) oxygen wherein X denotes at least one element selected from the group consisting of potassium, sodium, rubidium, lithium, cerium, beryllium, magnesium, calcium, vanadium, strontium, zinc, thorium and rhenium. The catalyst of the present invention has a long service life which is significantly superior to those of the prior phosphomolybdic acid-based catalysts.

It has surprisingly been found that the catalyst is stable at elevated temperatures, for example, at 600° C.

However, this catalyst as such is not completely satisfactory, because a part of phosphorus which is one of the essential components of the catalyst, though in a very small amount, leaves out of the catalyst system during the reaction. Consequently, the semi-eternal life required for commercial catalysts can not be attained.

The inventors have found that when the reaction is carried out in the presence of the catalyst, the catalyst can be stabilized and its service life can further be prolonged by continuously or intermittently supplementing phosphorus in an appropriate amount corresponding to that of the phosphorus which leaves out of the catalyst system.

The process of the present invention is epoch-making and of great value for commercial use since methacrylic or acrylic acid can be selectively produced in high yields for long periods of time.

The term "a phosphoric acid or a phosphorus compound capable of forming a phosphoric acid through a chemical change during the reaction" (hereinafter to be referred to as a phosphorus-containing compound) which is to be supplied to the reaction system in accordance with the present invention means any of phosphoric acids and phosphorus compounds capable of forming a phosphoric acid through a chemical reaction such as hydrolysis, oxidation, etc., including orthophosphoric acid, pyrophosphoric acid, metaphosphoric acid, phosphorous acid, hypophosphorous acid, phosphine, organic phosphoric acids, solid phosphoric acids, etc.

To the reaction system the phosphorus-containing compound may be supplied in any suitable manner.

For example, if the phosphorus-containing compound is water-soluble, it may uniformly be dissolved in water to be used for the reaction so that it is carried to the reaction system along with water.

If the phosphorus-containing compound is solid, for example, a solid phosphoric acid, this solid material may be charged in front of the catalyst layer. As steam is fed and made contact with the charged material, the latter generates a phosphoric acid, which is carried to the catalyst layer along with steam.

Furthermore, if the phosphorus-containing compound is gaseous, a gaseous mixture of the same and air may be fed to the catalyst layer.

The amount of the phosphorus-containing compound to be supplied may vary over a wide range. In general, the phosphorus-containing compound is supplied so that the amount of phosphorus contained in the compound is preferably 5 to $1 \times 10^{-4}$ wt%, more particularly 0.5 to $1 \times 10^{-3}$ wt% on the basis of a total amount of water fed during the reaction.

A preferred catalyst according to the present invention has the following composition;

$$Pd_aP_bSb_cX_dO_e$$

wherein X denotes at least one element selected from the group consisting of potassium, sodium, rubidium, lithium, cerium, beryllium, magnesium, calcium, vanadium, strontium, zinc, thorium and rhenium, the subscripts a, b, c, d and e denote the number of the Pd, P, Sb, X and O atoms, and wherein a is 1, b is 1 to 42, c is 0.1 to 15, d is 0.1 to 15 and e is a number determined by the valences of other elements and usually from 3.7 to 143.5.

A more preferred catalyst is a composition represented by the above formula in which the ratio among a, b, c, d and e lies in the following range: $a:b:c:d:e = 1:(1-28):(0.2-10):(0.1-10):(3.9-114.7)$.

The catalyst according to the present invention can be prepared in a conventional manner well known in the art, for example, by the following procedures.

In one case, compounds of respective constituent elements and the carrier, if a carrier is used, are mixed. The resultant mixture is evaporated to dryness and then the dried product is calcined.

In another case, a solid carrier is impregnated with compounds of respective constituent elements. This impregnated carrier is evaporated to dryness and then calcined.

In yet another case, a solid carrier is impregnated with compounds of some consituent elements and then subjected to a heat treatment, preferably at a temperature of 100–800° C. The partly impregnated carrier is further impregnated with compounds of the remaining constituent elements. This twice impregnated carrier is evaporated to dryness and then calcined.

In any of the above-described procedures the calcination temperature lies preferably in a range of 300–800° C., more preferably in a range of 350°–550° C.

If necessary, the calcination or the heat treatment may be carried out in an atmosphere of reducing agent such as hydrogen, hydrocarbon etc.

Examples of compounds of respective constituent elements are listed below.

Examples of palladium compounds include palladium chloride, nitrate and sulfate, palladium black and the like.

Examples of phosphorus compounds include orthophosphoric, pyrophosphoric, metaphosphoric, polyphosphoric, phosphorous and hypophosphorous acids and salts thereof and the like.

Examples of antimony compounds include oxides, hydroxides and chlorides of antimony such as antimony trioxide, trichloride and pentachloride and the like.

Examples of potassium, sodium, rubidium, lithium, cerium, beryllium, magnesium, calcium, vanadium, strontium, zinc, thorium and rhenium compounds include nitrates, hydrochlorides, phosphates, sulfates, oxides, hydroxides etc. of such elements.

More concrete procedures for the preparation of the catalyst are as follows.

To an aqueous ammonia solution of any suitable palladium salt, for example palladium chloride is added orthophosphoric acid, phosphorous acid, hypophosphorous acid or any other phosphoric acid or salt thereof, yielding a clean solution. To this clean solution are further added a solution of salt of X compound, for example, magnesium nitrate or magnesium phosphate, and antimony compound such as antimony oxide, hydroxide or chloride, for example, antimony trioxide, yielding a mixture. Any suitable carrier is impregnated with the above-described mixture, evaporated to dryness and then calcined in air at 300–800° C. for four or more hours.

The carrier which has been impregnated with a palladium compound such as palladium salt and thermally treated may be impregnated with a phosphorus compound, X compound and antimony compound and then calcined.

Or, the carrier which has been impregnated with X compound and antimony compound and thermally treated may be impregnated with an palladium compound and then calcined in air and thermally treated in an atmosphere of reducing agent. The resultant substance is impregnated with phosphorus compound and then calcined.

In any case the activity of the catalyst is not adversely affected.

The catalyst can include a carrier to lower the catalyst concentration, increase the catalyst strength or to enhance the economy of the catalyst.

As the carrier may be employed inert substances such as silica sol, silica gel, silicon carbide, α-alumina, Alundum, celite, boiling bubble stone, aluminum powder and the like.

The catalyst may be used in the form of spherical granules, pellets, particles crushed to suitable size, tablets etc.

Molecular oxygen is used for oxidizing methacrolein or acrolein in accordance with the present invention. To this end air is generally used. Pure oxygen may also be used alone or in admixture with an inert gas such as nitrogen, carbon dioxide and the like.

To the reaction system methacrolein or acrolein and oxygen are fed as a gaseous feed mixture in such proportions that the molar ratio of methacrolein or acrolein to oxygen is preferably 1: (0.5–30), more preferably 1 : (1–8).

The reaction between methacrolein or acrolein and oxygen is carried out in the presence of steam according to the process of the present invention. The presence of steam is indispensable to this reaction. If steam is absent, the oxidation of methacrolein or acrolein may occur to a very small extent or may not occur at all. In this aspect the catalyst according to the present invention is virtually different from known catalysts used for the oxidation of methacrolein or acrolein.

The steam is involved in the gaseous feed mixture in such proportions that the amount of steam is preferably 0.5 to 40 moles, more preferably 1 to 28 moles per mole of methacrolein or acrolein.

The temperature for carrying out the reaction is not so critical. The reaction may preferably be carried out at a temperature of 180° to 420° C., especially 200° to 390° C.

The reaction can be carried out at atmospheric pressure or at lower or higher pressures. In general it is convenient to carry out the reaction at atmospheric pressure. A preferable range of pressure is 0.3 to 15 atm.

The gaseous feed mixture can be introduced at any desirable space velocity, preferably at a space velocity of 300 to 15,000 l-gas/l-cat.hr, especially 700 to 8,000 l-gas/l-cat.hr.

According to the present invention satisfactory results are obtained even when the reaction is carried out at space velocities as high as 2,000 to 8,000 l-gas/l-cat.hr. Further the service life of the catalyst is maintained for a long period of time under such conditions.

The catalyst of the present invention may be applied in any form selected from a fixed bed, a fluidized bed and a moving bed.

The following examples are illustrative of the catalyst and the process of the present invention. In the examples, the terms "conversion of methacrolein or acrolein," "selectivity of methacrylic or acrylic acid," "yield of methacrylic or acrylic acid," and "space velocity" are defined as follows.

Conversion of methacrolein or acrolein =
$$\frac{\text{A number of moles of the reacted methacrolein or acrolein}}{\text{A number of moles of the fed methacrolein or acrolein}} \times 100\%$$

Selectivity of methacrylic or acrylic acid =
$$\frac{\text{A number of moles of the produced methacrylic or acrylic acid}}{\text{A number of moles of the reacted methacrolein or acrolein}} \times 100\%$$

Yield of methacrylic or acrylic acid =
$$\frac{\text{A number of moles of the produced methacrylic or acrylic acid}}{\text{A number of moles of the fed methacrolein or acrolein}} \times 100\%$$

Space Velocity (SV) =
$$\frac{\text{A flow rate}^* \text{ of a gaseous feed mixture (l-gas/hr)}}{\text{A volume of a charged catalyst (l-cat.)}}$$

*calculated on a basis at the normal temperature and pressure.

EXAMPLE 1

While 16.0 g of Aerosil (SiO$_2$) was heated and agitated, 0.4 g of antimony trioxide and 0.17 g of magnesium phosphate were added.

The mixture was concentrated by heating, then evaporated to dryness and thereafter, dried at 100° C. for eight hours. The dried mixture was impregnated with an aqueous ammonia solution containing 0.44 g of palladium chloride, evaporated to dryness, thereafter repeatedly washed with 10 liters of distilled water and dried. The dried product was subjected to a heat treatment in the air at 450° C. for five hours and then thermally treated in an atmosphere of hydrogen at 450° C. for five hours. The product was impregnated with 6.5 g of hypophosphorous acid, evaporated to dryness. Thereafter, the dried product was calcined in the air at 450° C. for five hours. The thus obtained product is named Catalyst A, the composition of which is represented by the formula:

$Pd_1P_{12.3}Sb_1Mg_{0.5}O_{33.75}$

A reaction tube of stainless steel having an inner diameter of 20 mm was filled with 10 ml of Catalyst A and dipped in a bath of molten nitrate. With the use of this reaction tube filled with Catalyst A the oxidation of methacrolein was carried out for 120 days.

As the phosphorus-containing compound was used trimethyl phosphate in the form of a 0.1% aqueous solution.

This aqueous solution was fed in an amount of 5cc per hour.

A gaseous feed mixture contained methacrolein, oxygen, steam, nitrogen and phosphorus in a relative molar ratio of $1:2:14:18.1:1.8\times10^{-3}$.

The gaseous feed mixture was supplied at a SV of 1565 l-gas/l-cat.hr.

The results of the reaction were as shown in Table 1. The yield of acrylic acid, acetic acid, carbon dioxide and carbon monoxide formed as the by-products in the conversion of methacrolein into methacrylic acid at the initial stage were 2.0%, 1.0%, 5.1% and 6.3%, respectively.

Table 1

| Reaction time (day) | Temperature of the nitrate bath (°C) | Conversion of methacrolein (%) | Yield of methacrylic acid (%) | Selectivity of methacrylic acid (%) |
|---|---|---|---|---|
| Initial stage | 300 | 78.5 | 64.5 | 82.2 |
| 40 | 300 | 78.7 | 64.7 | 82.2 |
| 120 | 300 | 78.7 | 64.5 | 82.0 |

EXAMPLE 2

Example 1 was repeated except that metaphosphoric acid in the form of a 0.1% aqueous solution was used as the phosphorus-containing compound in place of trimethyl phosphate.

Other reaction conditions were the same as those of Example 1. The results are shown in Table 2.

Table 2

| Reaction time (day) | Temperature of the nitrate bath (°C) | Conversion of methacrolein (%) | Yield of methacrylic acid (%) | Selectivity of methacrylic acid (%) |
|---|---|---|---|---|
| Initial stage | 301 | 77.8 | 63.7 | 81.9 |
| 40 | 301 | 77.9 | 63.5 | 81.5 |
| 120 | 301 | 77.9 | 63.7 | 81.8 |

The yield of acrylic acid, acetic acid, carbon dioxide and carbon monoxide formed as the by-products in the conversion of methacrolein into methacrylic acid at the initial stage were 3.1%, 1.0%, 5.0% and 6.0%, respectively.

EXAMPLE 3

A catalyst having the same composition as that of Example 1 was prepared similar to that of Example 1, except that hypophosphorous acid was replaced by phosphorous acid.

With the use of the catalyst the reaction was carried out in a similar manner as described in Example 1. The results are shown in Table 3.

Table 3

| Reaction time (day) | Temperature of the nitrate bath (°C) | Conversion of methacrolein (%) | Yield of methacrylic acid (%) | Selectivity of methacrylic acid (%) |
|---|---|---|---|---|
| Initial stage | 298 | 77.5 | 64.2 | 82.8 |
| 40 | 298 | 76.7 | 64.1 | 83.6 |
| 120 | 298 | 77.6 | 64.3 | 82.8 |

The yield of acrylic acid, acetic acid, carbon dioxide and carbon monoxide formed as the by-products in the conversion of methacrolein into methacrylic acid at the initial stage were 1.0%, 0.5%, 5.3% and 6.5%, respectively.

EXAMPLE 4

The reaction described in Example 1 was repeated except that acrolein was used in place of methacrolein. The results are shown in Table 4.

Table 4

| Reaction time (day) | Temperature of the nitrate bath (°C) | Conversion of acrolein (%) | Yield of acrylic acid (%) | Selectivity of acrylic acid (%) |
|---|---|---|---|---|
| Initial stage | 297 | 96.5 | 90.1 | 93.4 |
| 40 | 297 | 96.7 | 90.0 | 93.1 |
| 120 | 297 | 96.7 | 90.4 | 93.5 |

The yield of acetic acid, carbon monoxide, carbon dioxide and acetone formed as the by-products in the conversion of acrolein into acrylic acid at the initial stage were 1.0%, 2.4%, 2.0% and 1.0%, respectively.

EXAMPLE 5

The reaction was carried out under the same conditions as those of Example 1, except that the phosphorus-containing compound was not fed at all. The results are shown in Table 5.

EXAMPLE 6

The reaction was carried out under the same conditions as those of Example 4, except that the phosphorus-containing compound was not fed at all. The results are shown in Table 5.

Table 5

| Ex. No. | Reaction time (day) | Temperature of the nitrate bath (°C) | Conversion of methacrolein (%) | Yield of methacrylic acid (%) | Selectivity of methacrylic acid (%) |
|---|---|---|---|---|---|
| 5 | Initial stage | 299 | 78.7 | 64.1 | 81.4 |
|   | 10 | 299 | 77.9 | 61.3 | 78.7 |

| Ex. No. | Reaction time (day) | Temperature of the nitrate bath (°C) | Conversion of acrolein (%) | Yield of acrylic acid (%) | Selectivity of acrylic acid (%) |
|---|---|---|---|---|---|
| 6 | Initial stage | 296 | 95.5 | 89.7 | 93.9 |
|   | 10 | 296 | 90.1 | 83.1 | 92.2 |

EXAMPLES 7–48

Catalysts having the compositions shown in Table 6 were prepared in a manner similar to that described in Example 1, if necessary, using nitrates of rubidium, calcium, potassium, lithium, zinc, sodium, strontium, thorium, cerium and beryllium, ammonium metavanadate and rhenium chloride. With use of these catalysts the reactions were carried out under the same conditions as those of Example 1, except that the phosphorus-containing compound was not fed at all. The results are shown in Table 6.

Table 6

| Example No. | Catalyst composition | Temperature of the nitrate bath (°C) | Conversion of methacrolein (%) | Yield of methacrylic acid (%) | Selectivity of methacrylic acid (%) |
|---|---|---|---|---|---|
| 7 | $Pd_1P_1Mg_{0.3}Sb_1O_{5.3}$ | 250 | 79.5 | 50.0 | 62.9 |
| 8 | $Pd_1P_3Mg_{0.5}Sb_1O_{10.5}$ | 252 | 76.5 | 45.3 | 59.2 |
| 9 | $Pd_1P_9Mg_{1.0}Sb_2O_{27.5}$ | 263 | 75.5 | 56.5 | 74.8 |
| 10 | $Pd_1P_{15}Mg_{5.0}Sb_7O_{54}$ | 271 | 74.5 | 61.7 | 82.8 |
| 11 | $Pd_1P_{28}Mg_{10}Sb_{10}O_{96}$ | 278 | 71.5 | 58.5 | 81.8 |
| 12 | $Pd_1P_{10}Mg_{0.1}Sb_{0.2}O_{26.4}$ | 270 | 73.5 | 51.3 | 69.7 |
| 13 | $Pd_1P_{12}Rb_1Sb_1O_{33.5}$ | 277 | 74.7 | 61.5 | 82.3 |
| 14 | $Pd_1P_5Rb_{0.5}Sb_1O_{15.3}$ | 269 | 76.3 | 55.4 | 72.6 |
| 15 | $Pd_1P_{18}Rb_5Sb_4O_{50}$ | 281 | 75.3 | 52.1 | 69.2 |
| 16 | $Pd_1P_{24}Rb_1Sb_1O_{63}$ | 281 | 74.5 | 57.3 | 76.9 |
| 17 | $Pd_1P_{12}Ca_1Sb_1O_{33.5}$ | 274 | 76.5 | 62.3 | 81.4 |
| 18 | $Pd_1P_{21}Ca_{0.5}Sb_2O_{57}$ | 285 | 74.5 | 59.1 | 79.3 |
| 19 | $Pd_1P_{23}Ca_2Sb_3O_{65}$ | 291 | 72.3 | 54.3 | 75.1 |
| 20 | $Pd_1P_5Ca_{0.2}Sb_{0.6}O_{14.6}$ | 271 | 75.5 | 49.1 | 65.0 |
| 21 | $Pd_1P_{13}K_{0.5}Sb_1O_{35.3}$ | 273 | 75.6 | 60.5 | 80.0 |
| 22 | $Pd_1P_{20}K_1Sb_2O_{54.5}$ | 275 | 74.5 | 55.2 | 74.1 |
| 23 | $Pd_1P_{10}K_5Sb_2O_{31.5}$ | 268 | 70.2 | 43.1 | 61.4 |
| 24 | $Pd_1P_{28}K_9Sb_8O_{87.5}$ | 285 | 76.0 | 41.0 | 53.9 |
| 25 | $Pd_1P_{12}Zn_1Sb_1O_{33.5}$ | 287 | 74.9 | 59.5 | 79.4 |
| 26 | $Pd_1P_{21}Zn_2Sb_2O_{58.5}$ | 290 | 73.9 | 57.5 | 77.8 |
| 27 | $Pd_1P_{12}Na_1Sb_1O_{33}$ | 273 | 74.5 | 60.7 | 81.5 |
| 28 | $Pd_1P_{21}Na_{0.5}Sb_2O_{56.8}$ | 282 | 77.0 | 59.6 | 77.4 |
| 29 | $Pd_1P_{26}Na_5Sb_3O_{73}$ | 290 | 77.5 | 43.5 | 56.1 |
| 30 | $Pd_1P_5Na_{0.1}Sb_{0.5}O_{14.3}$ | 261 | 76.2 | 40.0 | 52.5 |
| 31 | $Pd_1P_{12}V_{0.5}Sb_1O_{33.3}$ | 267 | 73.5 | 62.2 | 84.6 |
| 32 | $Pd_1P_{21}V_1Sb_3O_{59.5}$ | 275 | 74.5 | 58.1 | 78.0 |
| 33 | $Pd_1P_5V_{0.2}Sb_5O_{21.3}$ | 263 | 72.6 | 40.1 | 55.2 |
| 34 | $Pd_1P_{12}Re_1Sb_2O_{36}$ | 250 | 77.5 | 63.1 | 81.4 |
| 35 | $Pd_1P_{23}Re_2Sb_1O_{64}$ | 260 | 78.2 | 60.1 | 76.9 |
| 36 | $Pd_1P_6Re_{0.3}Sb_{0.5}O_{17.4}$ | 241 | 75.6 | 53.2 | 70.4 |
| 37 | $Pd_1P_{12}Sr_{0.5}Sb_1O_{33}$ | 267 | 75.5 | 57.6 | 76.3 |
| 38 | $Pd_1P_{24}Sr_3Sb_2O_{67}$ | 278 | 73.1 | 56.9 | 77.8 |
| 39 | $Pd_1P_5Sr_5Sb_{0.5}O_{19.3}$ | 269 | 77.0 | 42.1 | 54.7 |

Table 6-continued

| Example No. | Catalyst composition | Temperature of the nitrate bath (°C) | Conversion of methacrolein (%) | Yield of methacrylic acid (%) | Selectivity of methacrylic acid (%) |
|---|---|---|---|---|---|
| 40 | $Pd_1P_{10}Th_1Sb_1O_{29.5}$ | 276 | 74.5 | 59.2 | 79.5 |
| 41 | $Pd_1P_{20}Th_3Sb_3O_{61.5}$ | 295 | 70.5 | 53.5 | 75.9 |
| 42 | $Pd_1P_4Th_{0.5}Sb_2O_{15}$ | 263 | 74.5 | 46.3 | 62.1 |
| 43 | $Pd_1P_{15}Ce_1Sb_1O_{40.5}$ | 279 | 74.3 | 57.5 | 77.4 |
| 44 | $Pd_1P_{20}Ce_2Sb_5O_{59.5}$ | 288 | 71.1 | 42.2 | 59.4 |
| 45 | $Pd_1P_{13}Be_1Sb_1O_{36}$ | 274 | 75.3 | 53.5 | 71.0 |
| 46 | $Pd_1P_{23}Be_2Sb_2O_{63.5}$ | 296 | 70.4 | 50.1 | 71.1 |
| 47 | $Pd_1P_{12}Li_1Sb_{0.6}O_{32.4}$ | 276 | 75.3 | 58.0 | 77.0 |
| 48 | $Pd_1P_{21}Li_2Sb_1O_{56}$ | 290 | 71.1 | 55.1 | 77.5 |

EXAMPLES 49–61

Catalysts having the compositions shown in Table 7 were prepared in a manner similar to those described in Examples 7–48. With use of these catalysts the reactions were carried out under the same conditions as those of Example 1. The results are shown in Table 7.

EXAMPLES 62–73

The reactions described in Example 4 were repeated except that catalysts having the compositions shown in Table 8 prepared in the same manner as in Examples 7–48 were used and the phosphorus-containing compound was not fed at all. The results are shown in Table 8.

Table 7

| Example No. | Catalyst composition | Reaction time (day) | Temperature of the nitrate bath (°C) | Conversion of methacrolein (%) | Yield of methacrylic acid (%) | Selectivity of methacrylic acid (%) |
|---|---|---|---|---|---|---|
| 49 | $Pd_1P_{12}Rb_1Sb_1O_{33}$ | 0 | 277 | 74.7 | 61.5 | 82.3 |
|  |  | 40 | 277 | 74.6 | 61.4 | 82.3 |
|  |  | 120 | 277 | 74.6 | 61.5 | 82.4 |
| 50 | $Pd_1P_{12}Ca_1Sb_1O_{33.5}$ | 0 | 274 | 76.5 | 62.3 | 81.4 |
|  |  | 40 | 274 | 76.6 | 62.2 | 81.2 |
|  |  | 120 | 274 | 76.5 | 62.3 | 81.4 |
| 51 | $Pd_1P_{12}K_{0.5}Sb_1O_{35.3}$ | 0 | 273 | 75.6 | 60.5 | 80.0 |
|  |  | 40 | 273 | 75.4 | 60.3 | 80.0 |
|  |  | 120 | 273 | 75.5 | 60.6 | 80.2 |
| 52 | $Pd_1P_{12}Na_1Sb_1O_{33}$ | 0 | 273 | 74.5 | 60.7 | 81.5 |
|  |  | 40 | 273 | 74.4 | 61.0 | 82.0 |
|  |  | 120 | 273 | 74.6 | 60.8 | 81.5 |
| 53 | $Pd_1P_{12}V_{0.5}Sb_1O_{33.3}$ | 0 | 267 | 73.5 | 62.2 | 84.6 |
|  |  | 40 | 267 | 73.4 | 61.9 | 84.3 |
|  |  | 120 | 267 | 73.4 | 62.0 | 84.5 |
| 54 | $Pd_1P_{12}Re_1Sb_2O_{36}$ | 0 | 250 | 77.5 | 63.1 | 81.4 |
|  |  | 40 | 250 | 77.5 | 62.9 | 81.2 |
|  |  | 120 | 250 | 77.4 | 63.1 | 81.5 |
| 55 | $Pd_1P_{12}Sr_{0.5}Sb_1O_{33}$ | 0 | 267 | 75.5 | 57.6 | 76.3 |
|  |  | 40 | 267 | 75.6 | 57.7 | 76.3 |
|  |  | 120 | 267 | 75.6 | 57.8 | 76.5 |
| 56 | $Pd_1P_{10}Th_1Sb_1O_{29.5}$ | 0 | 276 | 74.5 | 59.2 | 79.5 |
|  |  | 40 | 276 | 74.4 | 59.2 | 79.6 |
|  |  | 120 | 276 | 74.5 | 59.1 | 79.3 |
| 57 | $Pd_1P_{15}Ce_1Sb_1O_{40.5}$ | 0 | 279 | 74.3 | 57.5 | 77.4 |
|  |  | 40 | 279 | 74.1 | 57.3 | 77.3 |
|  |  | 120 | 279 | 74.2 | 57.4 | 77.4 |
| 58 | $Pd_1P_{13}Be_1Sb_1O_{36}$ | 0 | 274 | 75.3 | 53.5 | 71.0 |
|  |  | 40 | 274 | 75.3 | 53.6 | 71.2 |
|  |  | 120 | 274 | 75.3 | 53.5 | 71.0 |
| 59 | $Pd_1P_{12}Li_1Sb_{0.6}O_{32.4}$ | 0 | 276 | 75.3 | 58.0 | 77.0 |
|  |  | 40 | 276 | 75.4 | 58.2 | 77.2 |
|  |  | 120 | 276 | 75.4 | 58.1 | 77.1 |
| 60 | $Pd_1P_{12.3}Sb_1Mg_{0.5}Rb_{0.5}O_{34}$ | 0 | 297 | 77.6 | 61.1 | 78.7 |
|  |  | 40 | 297 | 77.5 | 61.2 | 78.9 |
|  |  | 120 | 297 | 77.6 | 61.0 | 78.6 |
| 61 | $Pd_1P_{12}Sb_{0.7}V_{0.5}K_{0.2}O_{33.4}$ | 0 | 271 | 74.5 | 60.0 | 80.5 |
|  |  | 40 | 271 | 74.4 | 60.0 | 80.6 |
|  |  | 120 | 271 | 74.5 | 60.2 | 80.8 |

Table 8

| Example No. | Catalyst composition | Temperature of the nitrate bath (°C) | Conversion of acrolein (%) | Yield of acrylic acid (%) | Selectivity of acrylic acid (%) |
|---|---|---|---|---|---|
| 62 | $Pd_1P_{12}Rb_1Sb_1O_{33.5}$ | 291 | 95.0 | 89.1 | 93.8 |
| 63 | $Pd_1P_{12}Ca_1Sb_1O_{33.5}$ | 296 | 94.2 | 88.5 | 93.9 |
| 64 | $Pd_1P_{13}K_{0.5}Sb_1O_{35.3}$ | 300 | 94.3 | 87.5 | 92.8 |
| 65 | $Pd_1P_{12}Na_1Sb_1O_{33.5}$ | 297 | 95.0 | 88.0 | 92.6 |
| 66 | $Pd_1P_{12}V_{0.5}Sb_1O_{33.8}$ | 299 | 96.0 | 89.7 | 93.4 |
| 67 | $Pd_1P_{12}Re_1Sb_1O_{33.5}$ | 289 | 97.0 | 90.0 | 92.8 |
| 68 | $Pd_1P_{12}Sr_{0.5}Sb_1O_{33}$ | 291 | 94.5 | 87.9 | 93.0 |
| 69 | $Pd_1P_{10}Th_1Sb_1O_{29.5}$ | 288 | 95.6 | 88.5 | 92.6 |
| 70 | $Pd_1P_{15}Ce_1Sb_1O_{40.5}$ | 283 | 90.5 | 85.9 | 96.0 |
| 71 | $Pd_1P_{13}Be_1Sb_1O_{36}$ | 291 | 97.0 | 89.0 | 91.8 |
| 72 | $Pd_1P_{12}Zn_1Sb_2O_{33.5}$ | 289 | 96.5 | 87.6 | 90.8 |

Table 8-continued

| Example No. | Catalyst composition | Temperature of the nitrate bath (° C) | Conversion of acrolein (%) | Yield of acrylic acid (%) | Selectivity of acrylic acid (%) |
|---|---|---|---|---|---|
| 73 | $Pd_1P_{12}Li_1Sb_{0.6}O_{32.4}$ | 282 | 95.7 | 88.1 | 92.1 |

EXAMPLE 74

The reactions described in Example 4 were carried out for 120 days using the same catalysts as in Examples 62–73. The results obtained after 120 days were nearly the same as those obtained at the initial stage. The yields of acrylic acid were not decreased for 120 days.

EXAMPLE ↓

Examples 1 and 4 were repreated except that solid phosphoric acid (celite/phosphorus = 50/50) heat treated at 550° C. was used as the phosphorus-containing compound in place of trimethyl phosphate.

On the upper side of the catalyst layer consisting of 10 ml of Catalyst A was placed 5 ml of the solid phosphoric acid.

The results were nearly the same as those of Examples 1 and 4.

EXAMPLE 76

Examples 49–61 and 74 were repeated except that orthophosphoric acid, metaphosphoric acid, pyrophosphoric acid and solid phosphoric acid were used as the phosphorus-containing compound in place of trimethyl phosphate, respectively, in each case. It has been found that the results are nearly the same as those of Examples 49–61 and 74.

EXAMPLE 77

Examples 1 and 4 were repeated except that the amount of the phosphorus-containing compound supplied was changed. The amount of phosphorus contained in the compound was changed in the range of 0.5 wt % to $1 \times 10^{-3}$ wt % based on an amount of water fed. The results were nearly the same as those of Examples 1 and 4.

EXAMPLE 78

A catalyst was prepared by following the procedure noted in Example 1, except that the impregnation order of palladium and phosphorus was changed. Using this catalyst the reactions were carried out in the same manner as in Examples 1 and 4. The results were nearly the same as those of Examples 1 and 4.

EXAMPLE 79

A catalyst was prepared by following the procedure noted in Example 1, except that palladium and phosphorus were impregnated at the same time. Using this catalyst the reactions were carried out in the same manner as in Examples 1 and 4. The results were nearly the same as those of Examples. 1 and 4.

EXAMPLE 80

16.0 g of Aerosil, 0.4 g of antimony trioxide, 0.17 g of magnesium phosphate, 6.5 g of hypophosphorous acid and 10 cc of an aqueous ammonia solution containing 0.44 g of palladium chloride were mixed together. The mixture was evaporated to dryness. The dried product was calcined in the air at 450° C. for five hours. The catalyst thus obtained had a composition represented by the formula: $Pd_1P_{12.3}Sb_1Mg_{0.5}O_{33.75}$ Using this catalyst the reactions were carried out in the same manner as in Examples 1 and 4. The results were nearly the same as those of Examples 1 and 4.

EXAMPLE 81

Example 1 was repeated except that the gaseous feed mixture was supplied at a SV of 4000 l-gas/l-cat.hr. The results are shown in Table 9.

Table 9

| Reaction time (day) | Temperature of the nitrate bath (° C) | Conversion of methacrolein (%) | Yield of methacrylid acid (%) | Selectivity of methacrylic acid (%) |
|---|---|---|---|---|
| Initial stage | 315 | 74.5 | 61.3 | 82.3 |
| 40 | 315 | 74.4 | 61.2 | 82.2 |
| 120 | 315 | 74.5 | 61.4 | 82.4 |

EXAMPLE 82

Example 4 was repeated except that the gaseous feed mixture was supplied at a SV of 4000 l-gas/l-cat.hr. The results are shown in Table 10.

Table 10

| Reaction time (day) | Temperature of the nitrate bath (° C) | Conversion of acrolein (%) | Yield of acrylic acid (%) | Selectivity of acrylic acid (%) |
|---|---|---|---|---|
| Initial stage | 307 | 92.1 | 86.2 | 93.6 |
| 40 | 307 | 92.3 | 85.9 | 93.1 |
| 120 | 307 | 92.2 | 86.0 | 93.3 |

What is claimed is:

1. A catalyst consisting essentially of the following composition:

$$Pd_aP_bSb_cX_dO_e$$

wherein X denotes at least one element selected from the group consisting of potassium, sodium, rubidium, lithium, cerium, beryllium, magnesium, calcium, vanadium, strontium, zinc, thorium and rhenium, the subscripts a, b, c, d and e denote the number of the Pd, P, Sb, X and O atoms, and wherein a is 1, b is 1 to 42, c is 0.1 to 15, d is 0.1 to 15 and e is a number determined by the valences of other elements and usually from 3.7 to 143.5.

2. A catalyst according to claim 1 wherein a is 1, b is 1 to 28, c is 0.2 to 10, d is 0.1 to 10 and e is 3.9 to 114.7.

* * * * *